(12) United States Patent
Allen et al.

(10) Patent No.: US 12,329,494 B2
(45) Date of Patent: Jun. 17, 2025

(54) INTEGRATED OPTICAL SYSTEM FOR SPECTRAL DOMAIN OPTICAL COHERENCE TOMOGRAPHY

(71) Applicant: SILOTON LIMITED, West Bridgford (GB)

(72) Inventors: Euan Allen, Bristol (GB); Alasdair Price, Bristol (GB)

(73) Assignee: Siloton Limited, West Bridgford (GB)

( * ) Notice: Subject to any disclaimer, the term of this patent is extended or adjusted under 35 U.S.C. 154(b) by 123 days.

(21) Appl. No.: 18/252,859

(22) PCT Filed: Nov. 15, 2021

(86) PCT No.: PCT/GB2021/052954
§ 371 (c)(1),
(2) Date: May 12, 2023

(87) PCT Pub. No.: WO2022/101643
PCT Pub. Date: May 19, 2022

(65) Prior Publication Data
US 2023/0414103 A1   Dec. 28, 2023

(30) Foreign Application Priority Data
Nov. 13, 2020 (GB) ...................... 2017937

(51) Int. Cl.
*A61B 5/05* (2021.01)
*A61B 5/00* (2006.01)
*A61B 3/10* (2006.01)

(52) U.S. Cl.
CPC ............ *A61B 5/0066* (2013.01); *A61B 3/102* (2013.01)

(58) Field of Classification Search
CPC .............................. A61B 5/0066; A61B 3/102
See application file for complete search history.

(56) References Cited

U.S. PATENT DOCUMENTS

2007/0237524 A1 * 10/2007 Gerstel ............... H04J 14/0284
398/83
2013/0308096 A1    11/2013 Engelhardt et al.
(Continued)

FOREIGN PATENT DOCUMENTS

JP     2017/111062 A    6/2017

OTHER PUBLICATIONS

International Search Report and Written Opinion dated Feb. 28, 2022 for Application No. PCT/GB2021/052954.
(Continued)

*Primary Examiner* — Joel F Brutus
(74) *Attorney, Agent, or Firm* — Knobbe, Martens, Olson & Bear, LLP (57) ABSTRACT

An apparatus for optical coherence tomography (OCT) scanning is described. The apparatus provides a first signal, a reference signal, a photonics integrated circuit, and a means for analyzing an interference signal. The photonics integrated circuit receives a reflected first signal, reflected from a subject. The photonics integrated circuit couples the reflected first signal to the reference signal to provide the interference signal. A variable delay, within the photonics integrated circuit, varies an optical path length of one of the reference signal and the first signal to match the optical path length of the reference signal to an optical path length of the reflected first signal. The variable delay includes at least one binary switch for selecting between paths of different lengths.

17 Claims, 7 Drawing Sheets

(56) References Cited

U.S. PATENT DOCUMENTS

| | | | | |
|---|---|---|---|---|
| 2014/0376000 | A1* | 12/2014 | Swanson | G01B 9/02091 |
| | | | | 356/479 |
| 2017/0227399 | A1* | 8/2017 | Hu | G02F 1/3136 |
| 2017/0238798 | A1* | 8/2017 | Isogai | A61B 3/1005 |
| 2017/0366880 | A1* | 12/2017 | Garcia | H04B 10/0799 |
| 2019/0257640 | A1 | 8/2019 | Avci | |
| 2020/0116489 | A1* | 4/2020 | Wang | G02B 6/29302 |
| 2021/0356249 | A1 | 11/2021 | Swanson | |

OTHER PUBLICATIONS

Zhou et al, "Integrated optical delay lines: a review and perspective [Invited]", Chinese Optics Letters, vol. 16, No. 10, Jan. 1, 2018 (Jan. 1, 2018), p. 101301.

Ji, et al., "On-Chip Tunable Photonic Delay Line", APL Photonics 4, 090803 (2019); https://doi.org/10.1063/1.5111164.

Rank, et al., "Spectral Domain and Swept Source OCT on a Photonic Integrated Circuit at 840nm for Ophthalmic Application", SPIE, European Conferences on Biomedical Optics, 2019, Munich, Germany, Proc. of SPIE-OSA vol. 11078 110780U-1 Downloaded From: https://www.spiedigitallibrary.org/conference-proceedings-of-spie on Aug. 4, 2020.

* cited by examiner

Directional coupler

Fig. 3a

Multimode interferometer (MMI)

Fig. 3b

Mach-Zehnder interferometer (MZI)

INTEGRATED OPTICAL SYSTEM FOR SPECTRAL DOMAIN OPTICAL COHERENCE TOMOGRAPHY

RELATED APPLICATIONS

This application is the U.S. National Phase of Application No. PCT/GB2021/052954 entitled "INTEGRATED OPTICAL SYSTEM FOR SPECTRAL DOMAIN OPTICAL COHERENCE TOMOGRAPHY" and filed Nov. 15, 2021, which claims the benefit of GB Patent Application No. 2017937.0, filed Nov. 13, 2020, each of which is incorporated by reference in its entirety.

FIELD OF THE INVENTION

This invention relates to apparatus and a method for performing optical coherence tomography, OCT, scanning, e.g. in the spectral domain, such as for ophthalmic purposes, e.g. for detecting factors that contribute to glaucoma. The invention seeks to implement an OCT scanner using photonic integrated circuit technology.

BACKGROUND

Optical coherence tomography (OCT) scanning is an imaging technique using low-coherent light to capture two- and three-dimensional images from within a media, for example the retina of an eye or other biological tissues, commonly used in ophthalmology. Different media have different absorption and reflective properties, therefore different wavelengths are absorbed and reflected off the various structures within a media, allowing a scan to be taken which can show these structures in the form of an image up to a depth of 1 or 2 mm. As biological tissues consist of mainly water (around 80%), light in the visible spectrum is conventionally utilized due to the respectively low absorption and scattering properties of water and therefore biological media.

A depth scan of a single point, or A-scan, is typically carried out using a light source characterized by a central wavelength, resulting in a unique spectrum from the reflected wavelengths corresponding to the structural properties of the media at the target point. A line scan consists of a line of point scans, or a B-scan, can be taken to obtain a cross-sectional scan of the media. An area scan, or a C-scan, consists of line scans in two different orthogonal axes, conventionally x- and y-axes, and results in a three-dimensional scan of the media.

An A-scan is typically performed by first splitting a single photonic input signal from an appropriate source into two signals. References herein to "splitting" a single photonic input signal include provision of two phase-locked signals, e.g. phase-locked lasers.

The splitting is preferably and approximately equal, whereby each split signal contains 50% of the power of the initial input signal, however this is not essential and the split may be uneven in the favour of the sample path, as will be explained. The splitting of the initial signal provides a measurement signal and a reference signal, which are transmitted on a sample path and reference path, respectively, and are reflected back along their respective paths. The respective path lengths are matched so that the path difference lies within the coherence length of the light source. The two signals are superimposed and an interference pattern is obtained. This pattern then undergoes spectral analysis, resulting in a spectrum corresponding to the point of the media that is being scanned.

OCT scanning can be carried out in the time domain (TD) or the frequency domain (FD). In the TD-OCT, the reference path length is varied in time to adjust the interference of the two split signals to obtain an output intensity that shows the reference mirror displacement against intensity. In the FD-OCT, the broadband interference of the two signals is obtained and a Fourier transform is applied to obtain a spectrum that shows depth against intensity. Two common approaches to FD-OCT scanning are spectral-domain (SD) and swept-source (SS) OCT. An example of an existing SD- and SS-OCT scanner on a photonics integrated circuit (PIC) for ophthalmic application can be seen in "Spectral domain and swept source optical coherence tomography on a photonic integrated circuit at 840 nm for ophthalmic application" by E. Rank at al. Proc. of SPIE-OSA Vol. 11078.

A problem with existing OCT apparatus is matching the reference path length to the sample path length.

Due to the individuality of the samples being tested, the sample path lengths between different samples differ for each individual. E.g. individuals have widely differing sizes (depths) of eyeball. Also, the presentation of the OCT apparatus to the user's eye can be subject to variation depending on the operator or manner of operation (e.g. depending on how the apparatus is offered up to the subject's face) and may be dependent on the shape of the subject's eye socket, cheekbone, forehead etc.

"On-chip tunable photonic delay line" by Xingchen Ji et al., APL Photonics 4, 090803 (2019) describes using ultralow loss high confinement $Si_3N_4$ waveguides with integrated microheaters as tunable delay lines on a chip. In order to achieve the variation in delay required an OCT apparatus, a variable delay line such as is described in this document needs to be very long. Very long optical delay lines can be problematic, in that they can introduce unwanted dispersion. They can also take up large chip areas due to the total length of the delay lines, and require the use of a considerable heating which can lead to problems with fibre connections, elongated settling times for the delay lines when changing delays, and can induce a level of instability on the chip.

Very small adjustments are required. With present technologies, only qualified individuals such as clinicians are adept at operating OCT apparatus. Less experienced or qualified individuals who are unable to gain assistance from qualified individuals are unable to carry out consistent and reliable OCT scans with compact and portable OCT scanning apparatus. This is a particular problem in extending the technology to use in developing countries.

SUMMARY OF THE INVENTION

According to the invention, an apparatus suitable for optical coherence tomography, OCT, scanning of a subject is provided, comprising: at least one source for providing a first signal and a reference signal, and a photonic integrated circuit. The photonic integrated circuit comprising: (i) a first path for receiving a reflected first signal, reflected from the subject; (ii) a second path for coupling the reflected first signal to the reference signal to provide an interference signal, and (iii) a variable delay for varying an optical path length of one of the reference signal and the first signal to match the optical path length of the reference signal to an optical path length of the reflected first signal, wherein the variable delay comprises a series of binary switches and path elements of different lengths of L, 2 L, etc. up to $2^n$ L, where N is an integer. A detector for analyzing and detecting the interference signal.

The first signal and the reference signal are preferably both light signals derived from a common light source.

The variable delay preferably acts on the reference signal, but could act on the first signal if an adequate fixed delay is also applied to the reference signal.

The delay component of the means for providing a variable delay may be a tunable spiral with integrated phase shifter or a tunable switch delay. A circular spiral has low curvature and is preferred, but alternatives to a spiral may be used, such as a serpentine pattern or other path condensed into a labyrinth.

The means for providing the first signal is preferably a broadband light source and the means for separating the interference signal spectrum is preferably a spectrometer. The spectrometer can be implemented as one of an arrayed waveguide grating, AWG, a ring bus, a ring fan-out, a binary asymmetric Mach-Zehnder interferometer, AMZI, or an AMZI fan out.

The means for providing the first signal may be a swept laser source, in which case the means for separating the interference signal spectrum can be a point photodetector, such as a complementary metal oxide semiconductor camera.

The means for providing the reference signal is preferably a beam-splitter, preferably splitting the first signal.

A first path within the PIC preferably guides the first signal to a set of imaging optics to the subject and guides reflected light from the subject back from through the set of imaging optics to the means for coupling. A second path within the PIC preferably guides the reference signal to a reflector and back to the means for coupling. The first and second paths preferably comprise polarization-maintaining fibres for maintaining polarization of the first signal and the reference signal respectively.

According to another aspect of the invention, a method suitable for performing an optical coherence tomography, OCT, scan is provided. The method comprises providing a first signal provided by a light source; providing a reference signal; reflecting the first signal from a subject and coupling the reflected first signal to the reference signal to provide an interference signal; adjusting a delay of one of the reference signal and the first signal by a variable delay to match an optical path length of the reference signal to an optical path length of the reflected first signal; and analyzing the interference signal. The step of adjusting comprises selecting between paths of different lengths.

The variable delay is preferably adjusted until an interference peak is identified in the interference signal. This may be achieved by performing image recognition on the interference signal to identify the interference peak.

The invention preferably performs FD-OCT scanning using a broadband interference of two signals. A Fourier transform is applied to interference signal to obtain a spectrum that shows depth against intensity.

Spectral-domain (SD) scanning is preferred, but swept-source (SS) scanning can be performed.

Preferred embodiments of the invention are now described, by way of example only, with reference to the accompanying drawings.

DETAILED DESCRIPTION OF THE DRAWINGS

Figure 1:
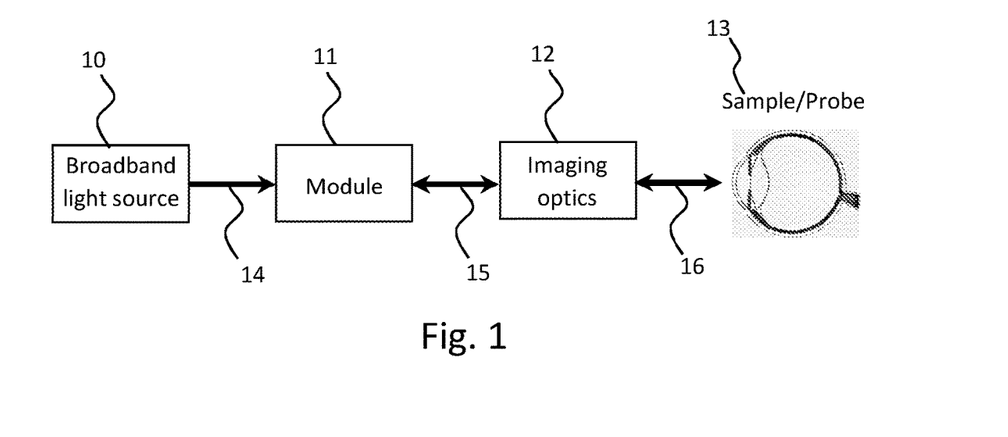
FIG. 1 shows a functional block diagram of an embodiment of an OCT scanner.

FIG. 1. is a functional block diagram of an example OCT scanner that is suitable for implementing various embodiments. FIG. 1 shows a broadband light source 10 that provides a photonic input signal to a photonic integrated circuit (PIC) module 11 via an optical port 14. The module 11 is optically connected to a set of imaging optics 12 by a polarization-maintaining (PM) fibre 15. The imaging optics 12 comprise a scanning unit containing two independent mirrors rotatable about perpendicular axes. The imaging optics 12 are coupled to a sample 13 such as a human eye via an undefined length of free space 16. In operation, a photonic input signal provided by the broadband light source 10 is transmitted to a port on the module 11. Polarization control at the light source is optional, but is unnecessary, for reasons explained below. The signal follows an optical path outwards from the module 11 through a PM fibre 15 to the imaging optics 12. The two independent mirrors of the imaging optics 12 control x and y-axial movements of the signal's path as it passes through the set of imaging optics 12. The path of the signal continues out of the imaging optics 12 and is incident upon the target sample 13. For a single point (e.g. a single pixel) of the output image, the signal reflects off the sample 13 and travels back through the set of imaging optics 12, and the PM fibre 15 to the module 11, where the signal is recorded and interpreted by the module 11.

Once a signal has been received by the module 11 from the set of imaging optics 12 and a point on the target has been captured, the described path of the signal repeats for another point or pixel. One of the x and y-axial mirrors in the imaging optics 12 (e.g. the x-axis mirror) adjusts its position for the next point or pixel, resulting in an output image for that pixel. This is repeated for a line to achieve a line scan of the sample 13. Then, the other mirror (the y-axis mirror) is incrementally rotated to direct the light to an adjacent line and the process is repeated for another line scan. When all lines have been scanned, a complete OCT 3D image of the target has been captured. Examples of such images for a fingerprint, a mouse ear and a human retina can be found in the above reference paper by E. Rank et al.

The scan can be a raster scan (of any suitable scanning pattern—steady-rate sweep or stairstep or otherwise), but it need not comprise individual pixels and can be continuous for a given line.

Figure 2:
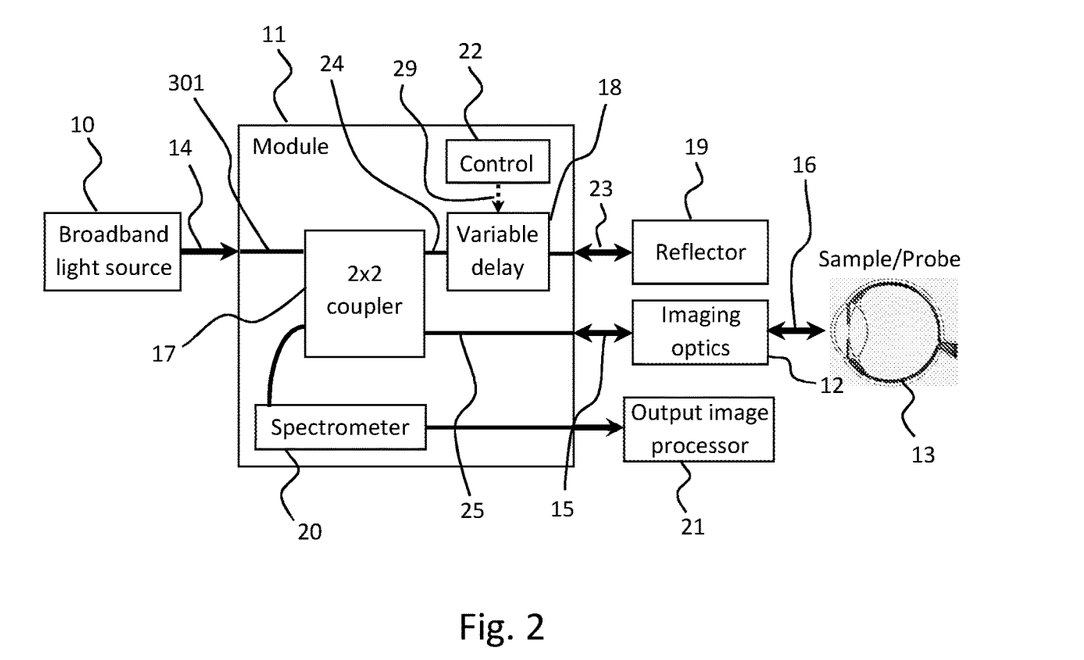
FIG. 2 shows a functional block diagram of a further embodiment of an OCT scanner with the constituents of the module shown.

The use of polarization maintaining fibre 15 and polarization maintaining fibre 23 obviates the need for polarization control on either or both of those arms.

As an alternative, single mode fiber (non-polarization preserving) can be used instead of PM fibre 15 and PM fibre 23. In this case, transmission down the fibre will cause a rotation in polarization resulting in a non-optimal operation of the module or integrated components. A polarization controller on or off the integrated device can be used to counteract the rotation in the fiber.

FIG. 2 is a functional block diagram of a further example OCT scanner that is suitable for implementing various embodiments. As above, the broadband light source 10 provides a photonic input signal to the module 11. The module 11 has a 2×2 coupler 17 which splits the initial input signal into two signals. One of the split signals is transmitted along an internal path 24 to a variable delay 18. The variable delay 18 is controlled by an internal control module 22 via a control path 29. The split signal continues along a PM fibre 23 to a reflector 19 (preferably a mirror) where the signal is reflected back to the path provided by the PM fibre 23, the variable delay 18, and internal path 24 to the 2×2 coupler 17. Meanwhile, the other split signal is transmitted along an internal path 25 leading into a PM fibre 15 to the imaging optics 12. The split signal is transmitted along an undefined length of free space 16 wherein the signal is incident upon the target sample 13. The signal is reflected back through the path provided by the set of imaging optics 12, PM fibre 15, and an internal path 25 to the 2×2 coupler 17.

At the coupler 17, the two received signals interfere with each other and the resultant signal is passed to a spectrometer 20. The spectrometer 20 analyses the spectral content of the received signal. It gives an analog or digital value of intensity for different wavelengths across the desired spectrum (which preferably encompasses the entire visible spectrum, but may extend into the IR spectrum or the UV spectrum). The spectral content is delivered to output image processor 21 to produce an image, which can be displayed on a display of the image processor 21 or can be analysed by that processor or can be stored and sent for remote viewing. The processor 21 builds up the image, because it "knows" the position of the x and y mirrors of the imaging optics. I.e. it has control of the scanning of the target and receives back the complete spectral results for each point/pixel/line of the scan, so it is able to build the image from the results for each spatial position it selects.

The splitting of the broadband light from the source 10 by the 2×2 coupler 17 into two signals is preferably and approximately equal split, whereby each split signal contains 50% of the power of the initial input signal, but this is not essential and the split may be uneven, with a greater proportion passing to the imaging optics (which is a more lossy path) and a lesser proportion to the reflector 19. Thus, it may be a 60:40 split or a 70:30 split or a 80:20 split or even a 90:10 split in favour of the imaging path.

As explained, one of the split signals is transmitted along internal path 24 to variable delay 18. This path provides a reference signal. The variable delay 18 is predefined by an individual using the internal control module 22 via a control path 29 to adjust for the individual's unique signal path length from the set of imaging optics 12 to the sample 13, as will be explained.

The reference signal travels a set distance from the coupler 17 to the reflector 19, therefore has a corresponding set delay. The signal from the target sample 13 has unique delay which corresponds to the distance from the coupler 17 to the imaging optics 12 summed with the undefined length of free space 16 to the target sample 13. The coupler 17 combines the two received split signals, producing an interference signal. The interference signal is transmitted to the spectrometer 20, where an internal interferometer compares the cross-correlation of the interference signal.

For the signals to interfere, they must be within one coherence length, and peak interference occurs when the two split signal path lengths match. Due to the interference level observed, the additional delay due to the undefined length of free space 16 can be determined by the spectrometer 20, allowing the delay of the reference signal path to be approximately matched to the target signal path.

In some embodiments, the information inferred from said comparison can be used to provide a manual adjustment to the variable delay 18 to match the reflector path length to the target sample 13 path length. This allows the user (e.g. an optometrist viewing an image produced by the image processor 21) to adjust the delay to increase the clarity of the image.

The optometrist may view the image remotely (e.g. over the Internet) and have remote control over the variable delay 18.

This ability to adjust the variable delay 18 for each individual patient means the optometrist can keep the physical apparatus of the OCT scanner in the same position and not have to adjust it for each individual patient. The imaging optics 12 can be made portable and robust for use "in the field" in ways in which the allow inexperienced operators to hold the optics to the eye of a patient with less strict requirements for head position and eye position. Greater variation of head and eye position can be tolerated by virtue of the ability to adjust the on-chip variable delay.

A further example could be the implementation of an adaptive learning or artificial intelligence imaging program to adjust the variable delay 18. For example, the program could scan an individual's eye making adjustments to the variable delay until the resultant image is recognizable as an interference pattern and, in particular, as the pattern for peak interference. In this way, the delay of both split signals approximately match according to a pre-defined threshold.

The individual's data could be stored so that if that individual were to be scanned again, the program could immediately adjust the variable delay 18 to their specific and unique path length.

Figure 3A:
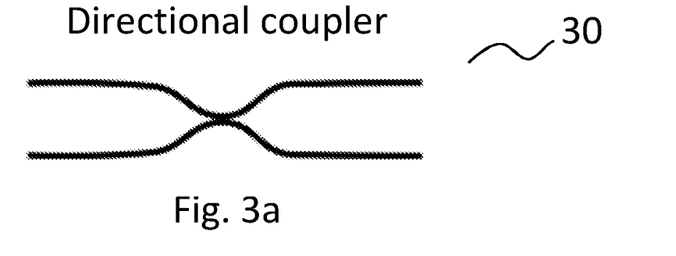
FIGS. 3a, 3b, and 3c show the embodiments of the 2×2 coupler of FIG. 2.
Figure 3B:
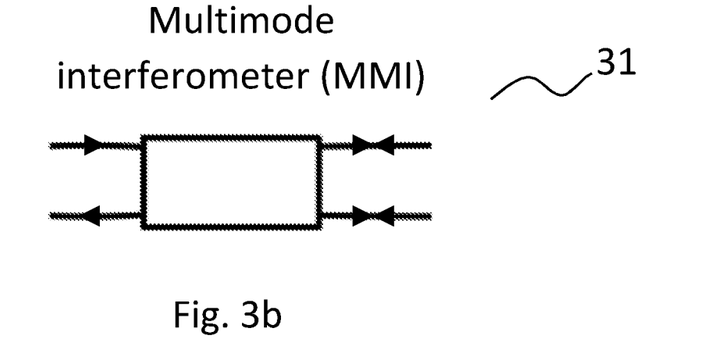
Figure 3C:
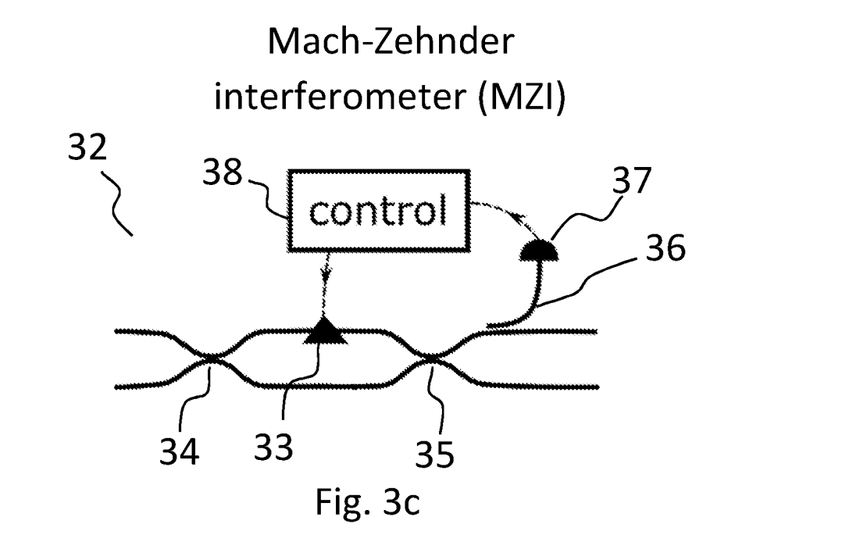

Various embodiments of the 2×2 coupler 17 are illustrated in FIGS. 3a, 3b, and 3c. With reference to FIGS. 3a-3c, a coupler 17 may include at least one of a directional coupler 30, a multimode interferometer (MMI) 31, and a Mach-Zehnder interferometer (MZI) 32 with an integrated phase shifter 33.

With reference to FIGS. 3a-3c, the directional coupler 30 and MMI 31 split or combine/interfere incoming optical signals. An incoming signal is split to at least two output signals with regards to its optical power. The ratio of the split is predefined by the fabrication and design of the directional coupler or MMI 31. The combination of at least two incoming signals produces output signals having the summed power of all input signals with a distribution in power at the output dependent on the optical phase difference between the incoming paths.

The MZI 32 introduces a variable phase difference via a phase shifter 33 between two collimated or waveguided optical signals, originally split from a single light source, between the two intermediary internal paths of the MZI 32.

In some embodiments, the coupler 17 may be comprised of an MZI 32, wherein the MZI 32 may have two balanced 2×2 couplers 34 and 35, wherein the couplers may be directional couplers 30 or MMIs 31, a tap waveguide 36, a photodetector 37, and an internal control feedback block 38.

In operation, a photonic input signal from the broadband light source 10 is transmitted to the module 11 and to the coupler 17 embodied by an MZI 32. The power of the split signals is described above.

Each split signal travels to internal paths 24 and 25 respectively. When the split signals return from their respective paths to the reflector 19 and to the target sample 13, they each travel into the MZI 32.

The MZI 32 may be used as a tunable 2×2 coupler, capable of offering a tunable splitting ratio between the two input and output optical modes.

Within the MZI 32, the intermediary phase shifter 33 controls the splitting ratio and induces a phase difference between the two intermediary internal paths of the MZI 32 which transmit the two incoming signals respectively. The tap waveguide 36 takes a small amount of the signal (typically around 1%) out of the 2×2 coupler 35 and sends it to a photodetector 37 where the optical power phase is measured. This measurement allows the splitting ratio of the MZI 32 to be inferred. This information is then fed back into the feedback control block 38 and is used to optimize the splitting ratio, and therefore phase, in the MZI 32 interference signal.

The phase shift may be performed via an electronically controlled change in the guiding material's refractive index using the internal control feedback block 38. For example, the change in the guiding material's refractive index may be carried out thermo-optically (using a heater), by using carrier effects (using an active carrier depletion or insertion region), by micro-electromechanical systems (MEMs), or by any other means of refractive index change.

Once the two signals have been combined, an interference is obtained. This resulting interference signal is transmitted out of the MZI 32 to the spectrometer 20.

In this way, the MZI provides a tuneable splitting ratio for the 2×2 coupler. Its 'total' operation is the same as a MMI or directional coupler (i.e. it interferes and splits two signals), but the MZI configuration allows for tuning of the splitting ratio via the intermediary phase shifter. In principle, the splitting can be tuned from 100:0 to 0:100.

Figure 4:
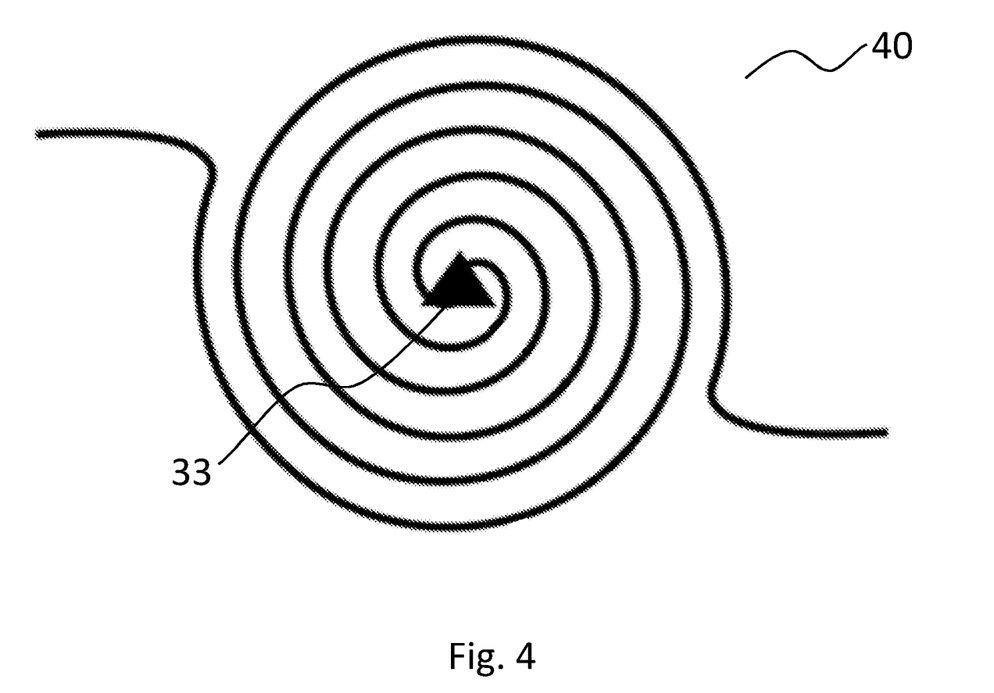
FIGS. 4 and 5 show the embodiments of the variable delay of FIG. 2.
Figure 5:
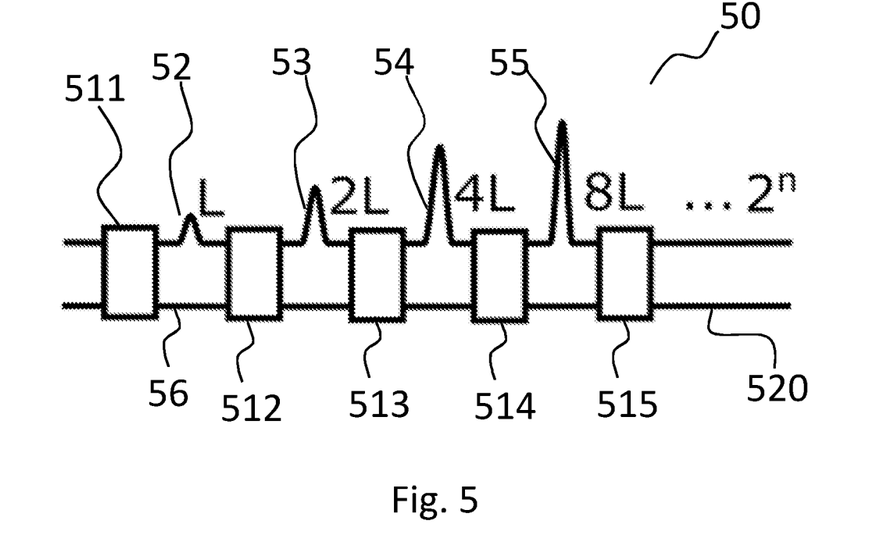

Various embodiments of the variable delay 18 are illustrated in FIGS. 4 and 5. FIG. 4 shows a tunable spiral waveguide 40 with at least one integrated phase shifter 33. The spiral shaped path of the waveguide 40 provides an additional predefined path length to the reference signal arm of the module 17 and so provides an initial delay which approximates the average length free space 16 to the target sample 13. The temperature of the waveguide can be adjusted by an on-chip heater to lengthen or shorten the path length of the spiral waveguide 40, thereby increasing or decreasing the additional delay applied to the reference signal.

The induced delay can be expressed in terms of a fixed delay and a fine/tuning delay. The fixed delay may approximately match the optical path of fibre 13 to the sum of the path lengths of the imaging optics 12, and probe paths 15 and 16. The fixed delay is typically about 40-60 cm but may be longer if the imaging optics are not co-located with the rest of the apparatus. The fine/tuning delay needs to achieve variation in path length of the order of 10s of mm, e.g. up to 80 mm, although a lower range is still very useful (e.g. 10-20 mm) depending on the application. These ranges are typical required in OCT systems. The fine/tuning delay may be implemented in steps of approximately 1 mm or less and is adjusted to provide incremental changes in the total delay.

If only one phase shifter 33 is present, this covers a section of path of the waveguide 40 path at its center and forms an 'S' shape. This applies a phase shift to any signal that passes through. If multiple phase shifters are present, they may be distributed arbitrarily along the path of the waveguide 40.

FIG. 5 shows a binary delay 50 with several integrated tunable switches 511, 512, 513, 514, and 515 where 'L' stands for a pre-defined unit delay. The upper 'rail' on the binary delay 50 have fibre optic, free space, or integrated photonic delay lines 52, 53, 54, and 55 of lengths L, 2 L, 4 L, and 8 L respectively between each tunable switch 511, 512, 513, 514, and 515 that may have an order of magnitude of $2^n$ which correspond to delays of $2^n$ unit delays, where n is a positive integer. The lower rail adds no significant delay to the path length comprised of non-delay path elements 56. The combination of the two rails results in a reprogrammable path length, wherein a desired delay to the reference signal can be implemented.

In operation, the multiple of L is calculated for a desired delay, and the tunable switches are configured so that the signal travels a path length matching the desired delay.

The length L and number of delays n depend on the minimum and maximum tuning length desired for the optical delay. L is preferably of the order of 0.1 mm to tens of millimetres, preferably about 0.5 mm-20 mm, more preferably 1 mm-10 mm.

For example, L may be approximately 0.5 mm, therefore if a 5 mm delay is desired, the programmed path length would be 10 L long. In this example, the binary delay 50 could be programmed so that the signal travels along delay lines 52 and 54, which would introduce delay path elements of length $2^0$ L and $2^2$ L to a total of 5 L. The returning light will follow the same path, so the total delay introduced is, in this case, 10 L or 5 mm.

In another example, again supposing a value for L of 0.5 mm, if a 20 mm delay is desired, the programmed path length would be 40 L long. The binary delay 50 can be preprogrammed so that the signal travels along delay lines 54 (or $2^2$ L) and $2^4$ L, where the delay line $2^4$ L is not shown. Again, the returning light will follow the same path, so the total delay introduced is, in this example, 20 mm.

The switches may also be non-MZI in operation, e.g. where the waveguide connections are physically moved and therefore switched.

The tunable switches 511, 512, 513, 514, and 515 are like individual two-way switches. Each MZI allows switching (selection, via the phase shift) to the bottom or top output of the MZI. By tuning the phase shift it is possible to switch from 100:0 or 0:100 (i.e. switch between the two outputs). They operate by heating the switches 511, 512, 513, 514, and 515 to change the signal path from the lower rail to the upper rail, wherein the default setting of the switches 511, 512, 513, 514, and 515 (i.e. when no heat is applied) is to transmit the signal along the lower rail, or vice versa. Alternatively, the tunable switches may also be operated by heating switches 511, 512, 513, 514, or 515 to change the signal path from its current rail to the other.

In the case where delay line 55 is the last switchable delay, the last switch 515 acts as a demultiplexer to bring the signal to the output 520.

Of course, there may be fewer or more switches and fewer or more delay path elements and they need not be arranged in length order.

There may be a need to switch from one to many different outputs/delay lengths (a multiplexer). Multiplexers can be many cascaded MZIs that 'fan-out' to many optical paths or more complex N×N MZI structures (rather than a simple 2×2). Each of these (2×2 MZIs and N×N MZIs) will be controlled by a phase shift as described above.

Switchable delay elements that select between paths of different lengths are advantageous over other variable delay arrangements because the total length of the delay line is reduced, thus reducing dispersion and the size of the chip and because the number of heaters needed to be active at any one time is reduced, thus again reducing dispersion, reducing the settling time for the delay line when changing delay paths, and increasing the stability of the chip.

In some embodiments, a combined version of the binary delay 50 and the tunable spiral waveguide with at least one phase shifter configurations could also be implemented in the variable delay 18. The binary delay 50 is preferably used to coarsely tune the variable delay 18 and the tunable spiral waveguide 40 with at least one phase shifter is preferably used to fine tune the variable delay 18, but the binary delay 50 and tunable spiral waveguide 40 with at least one phase shifter could be configured to both coarsely tune the variable delay 18, both fine tune the variable delay 18 or for the binary delay 50 to fine tune the variable delay 18 and the tunable spiral waveguide 40 with at least one phase shifter to coarse tune the variable delay 18.

Figure 6:
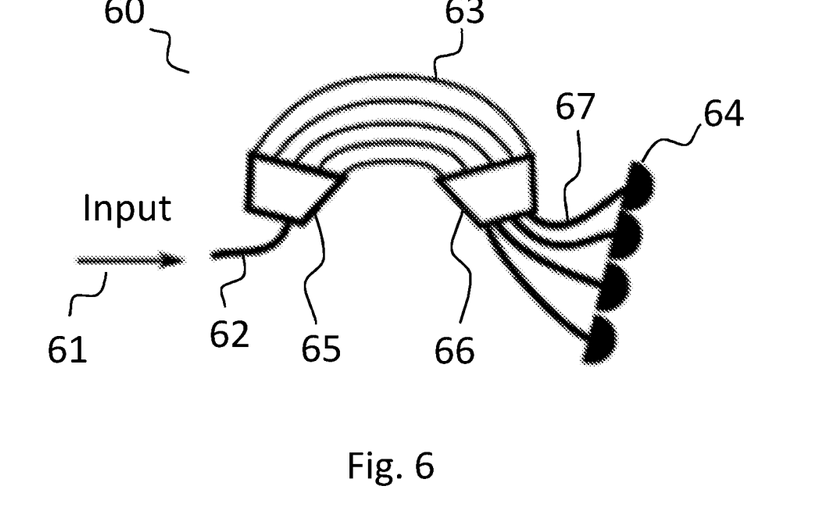
FIG. 6 shows an arrayed waveguide grating (AWG), an embodiment of the spectrometer.

Various embodiments of the spectrometer 20 are shown in FIGS. 6-10. FIG. 6 shows an arrayed waveguide grating (AWG) 60 with an input waveguide 62 and a set of photodetectors 64 leading on from the output waveguides 67. The incoming input signal 61 is transmitted to an array of integrated waveguides 63 via a free propagation region (FPR) 65. The waveguides are of different lengths and therefore apply different phase shifts to the input signal 61, thereby separating the different wavelengths of the signal at the second FPR 66. These now-separated wavelengths are received by an array of output waveguides 67 which lead onto the set of photodetectors 64. Each photodetector 64 receives a different wavelength. Thus, the set of photodetectors displays the spectrum of the input signal 61.

Figure 7:
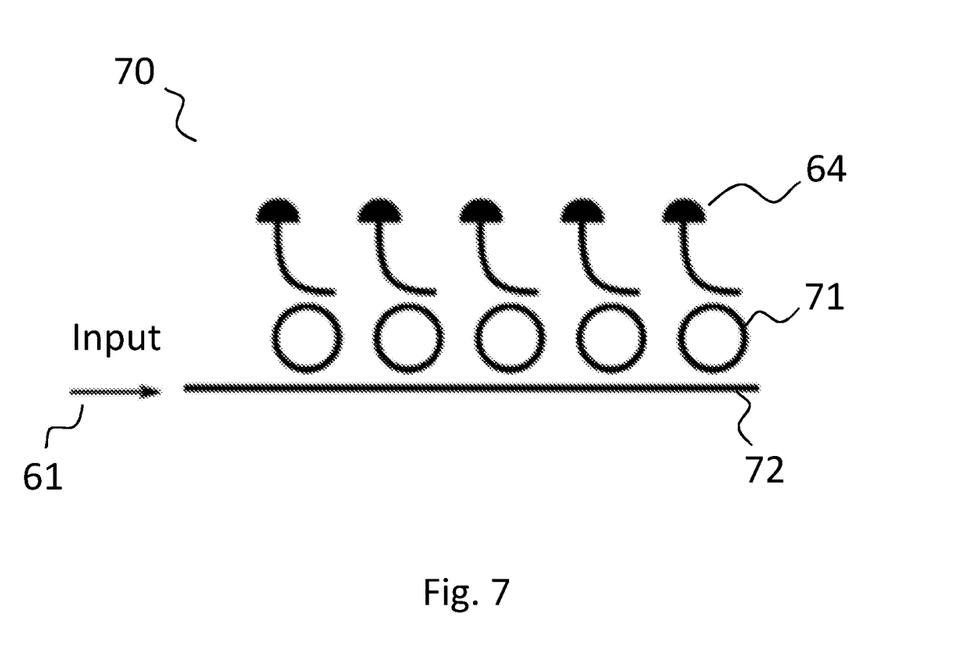
FIG. 7 shows a ring bus, an embodiment of the spectrometer.

FIG. 7 shows a ring bus 70 with an input 61 and a linear arrangement of photodetectors 64 situated above a parallel linear arrangement of optical ring resonators 71, where one optical ring resonator 71 is paired with one photodetector 64. When the signal enters each ring resonator 71, cavity resonance effects within the individual ring resonators 71 result in only certain wavelengths of the signal being supported. The properties, for example length or refractive index, of each ring resonator 71 differ from one to the next, such that each ring resonator 71 selectively picks off particular wavelengths from the input signal 61 as it travels along the bus waveguide 72. The collection of rings allows for measurement of the spectrum of the input signal 61 to be gathered via an array of photodetectors, with each photodetector paired with one ring resonator 71.

Figure 8:
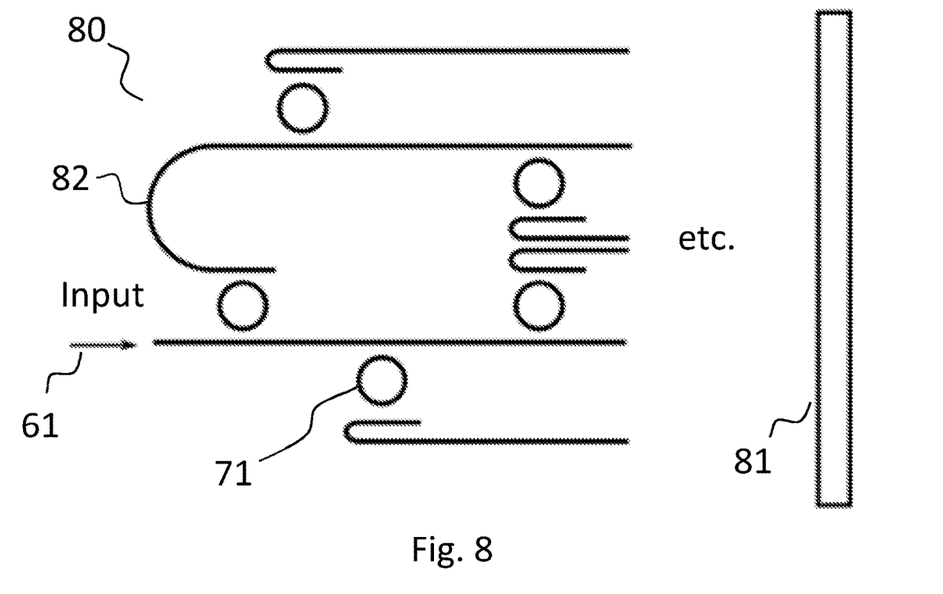
FIG. 8 shows an example configuration for a ring fan-out, an embodiment of the spectrometer.

FIG. 8 shows an example configuration for a ring fanout 80 comprising a cascade of optical ring resonators 71 connected via internal optical waveguides 82 leading to a photodetector array 81. An input signal 61 is incident upon the first ring resonator 71, where some of the wavelengths contained within the input signal 61 are separated from the main input signal 61 path due to resonant effects, as described above. The signal propagates through the cascade of ring resonators 71 via the internal optical fibres 82 until the wavelengths have been separated to a pre-defined degree of separation. The separated wavelengths are then incident upon the photodetector array 81 where the spectrum is obtained.

An advantage of a ring bus or a ring fanout spectrometer lies in its ease of manufacture on an integrated circuit. The rings can be made to an accurate size to resonate at specific selected wavelengths of light. They are therefore reproducible, reliable and robust.

Figure 9:
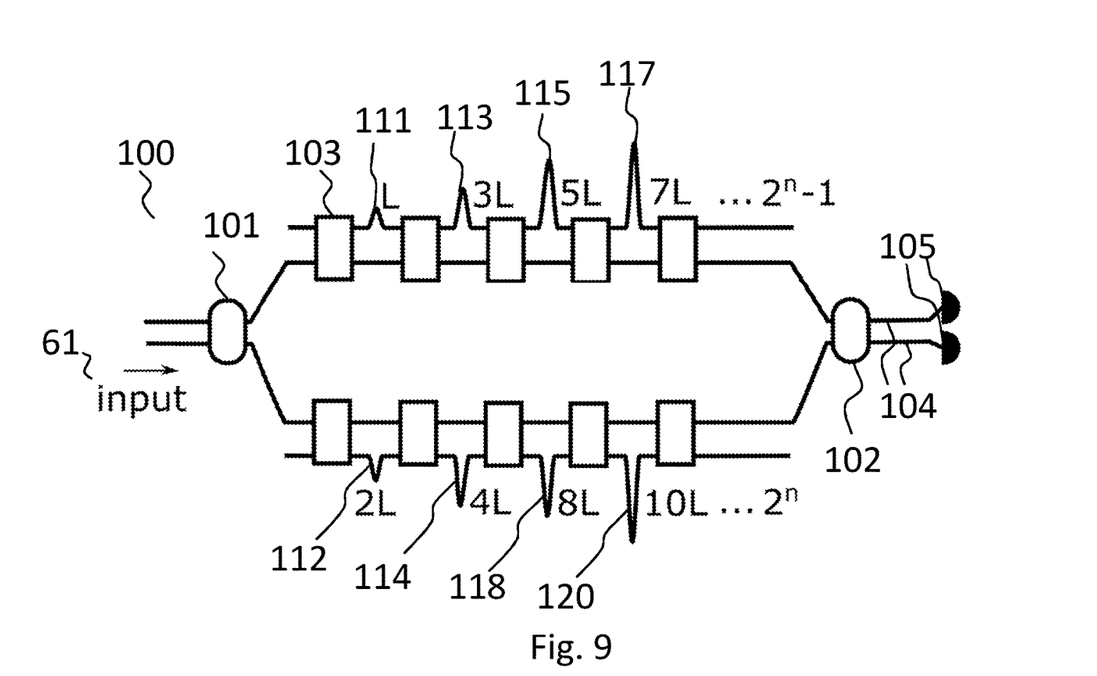
FIG. 9 shows a binary asymmetric Mach-Zehnder interferometer (AMZI), an embodiment of the spectrometer.

FIG. 9 shows a binary asymmetric Mach-Zehnder interferometer (AMZI) 100 with 2×2 optical couplers 101 and 102 and two 'banks' of integrated tunable switches 103 separated by asymmetric delay lines 111, 113, 115, and 117 on the upper bank and delay lines 112, 114, 118, and 120 on the lower bank, defined by a pre-defined unit delay 'L', similar to FIG. 5. The magnitude of the delay path can be up to $(2^n-1)L$ on the upper bank and $2^n L$ on the lower bank. The output signal is detected by a small array of photodetectors 105 via branches at the output 104.

In operation, an input signal 61 is split by the first 2×2 coupler 101 by a predetermined ratio, wherein the ratio may be 50/50. Each split signal travels along a preprogrammed asymmetric path length comprised of a bank of tunable switches 103 separated by delay lines 111, 113, 115, and 117 on the upper bank or 112, 114, 118, and 120 on the lower bank, wherein each delay line has a different length and so a different preset delay. The process of changing the signal path length is similar to FIG. 5. The now asymmetrically delayed two split signals are recombined at another 2×2 coupler 102 and are transmitted to a small array of photodetectors 105. The recombination of the split signals at the 2×2 coupler 102 causes interference, resulting in only specific wavelengths to be transmitted along each branch of the output 104. By tuning the asymmetry of the path delays of the two split signals, different wavelengths can be observed, thus a spectrum of the input signal 61 can be obtained. For example, the spectrum may be obtained using Fourier-transform spectrometer computational methods.

Figure 10:
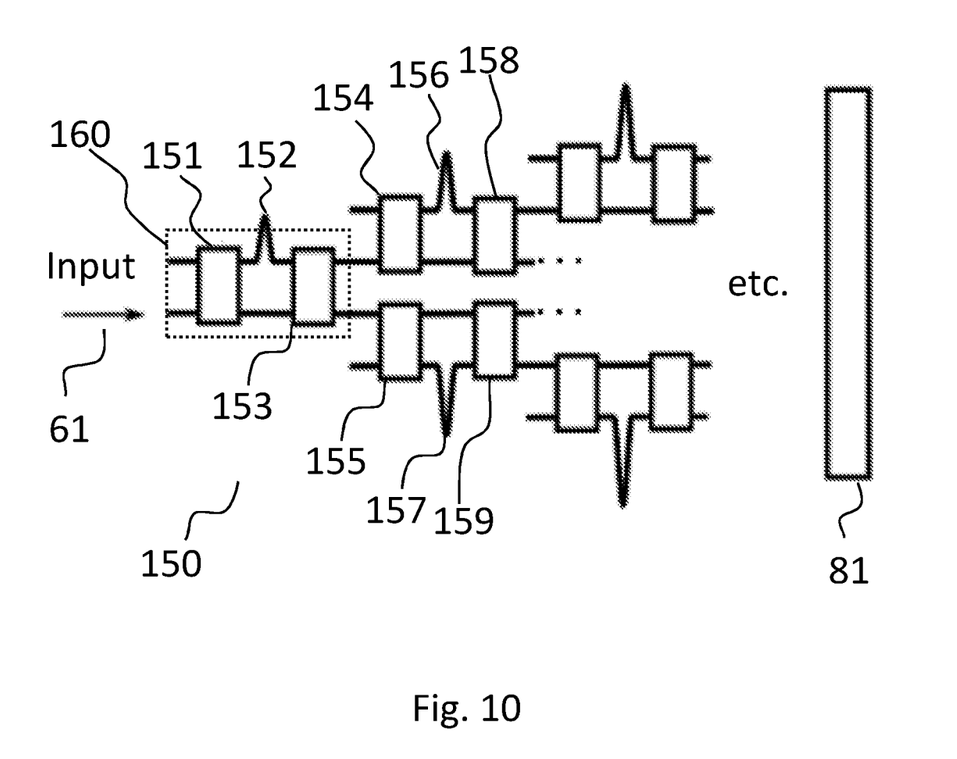
FIG. 10 shows an AMZI fan-out, an embodiment of the spectrometer.

FIG. 10 shows an AMZI fan-out 150 with integrated optical couplers 151, 153, 154, 155, 158, and 159, separated by delay lines 152, 156, and 157, an input 61 and a photodetector array 81. For example, the first AMZI 160 is shown to comprise an input optical coupler 151, a delay line 152, and an output optical coupler 153. Each AMZI 160 has two outputs which lead to two subsequent AMZIs 160. This structure continues until reaching the final set of AMZIs, where the outputs correspond to individual photodetectors in the photodetector array 81.

Each AMZI 160 is set to a different asymmetry, similar to the range of asymmetries described for FIG. 9, such that any particular wavelength at the input 61 has a unique path through the AMZI fan-out 100 and therefore reaches a particular photodiode in the photodetector array 81. By measuring each photodiode in the array 81, reconstruction of the spectrum at the input 61 can be completed.

A binary AMZI has the advantage that it is low loss due to the simplicity of required components and requires only one or two output photodiodes in contrast to an entire photodetector array. A fan-out AMZI 100 expansion also allows for low loss measurement of the spectrum due to the simplicity of components over multi-modal devices, and also allows for instantaneous retrieval of the input spectrum without any complex computational analysis.

In some embodiments, a combined version of any of the multiple devices described in FIGS. 6-10 may be used to implement the spectrometer.

Figure 11:
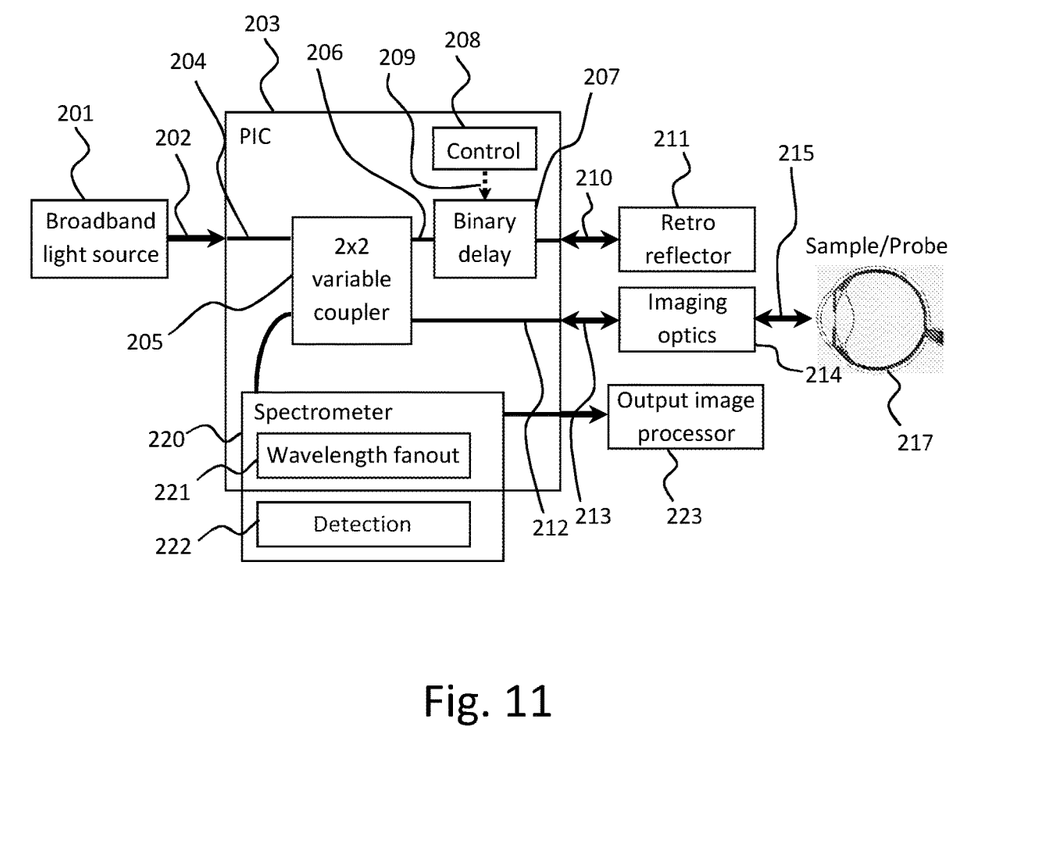
FIG. 11 shows a functional block diagram of further embodiment of an OCT scanner with the constituents of the photonic integrated circuit (PIC) shown.

FIG. 11 is a functional block diagram of a further example OCT scanner that is suitable for implementing various embodiments. As previously explained, the broadband light source 201 provides a photonic input signal to the module 11, embodied by a photonic integrated circuit (PIC) 203. The PIC has a 2×2 variable coupler 205 which splits the initial input signal which travels via an internal path 204 into two signals. One of the split signals is transmitted along the internal path 206 to the variable delay 18, embodied by a binary delay 207. The binary delay 207 is controlled by the internal control module 208 via the control path 209. The split signal continues along the PM fibre 210 to the reflector, embodied by a retro reflector 211 where the signal is reflected back to the path provided by the PM fibre 210, the binary delay 207, and internal path 206 to the 2×2 variable coupler 205. Meanwhile, the other split signal is transmitted along the internal path 212 leading to the PM fibre 213 to the imaging optics 214. The split signal is transmitted along the undefined length of free space 215 wherein the signal is incident upon the target sample 217. The signal is reflected back though the path provided by the set of imaging optics 214, PM fibre 213, and internal path 212 to the 2×2 variable coupler 205.

At the variable coupler 205, the two received signals interfere with each other and the resultant signal is passed to the spectrometer 220. The method by which the spectrometer 220 prepares the incoming resultant interference signal is shown by the internal modules of the spectrometer 220 which comprise a wavelength fanout 221 and a detection 222 module. These internal modules are also embodied by FIGS. 6-10.

An example method of demultiplexing an interference signal to obtaining the interference pattern is to use one or more asymmetric Mach-Zehnder Interferometers (AMZIs). An AMZI first splits an input signal using a waveguide and transmits the split signals along two optical delay lines of different lengths then recombines them using a second waveguide. The path difference between the delay lines can be defined by $\Delta L = m\lambda_c/\eta_{\mathit{eff}}$, where m is the order, $\lambda_c$ is the center wavelength of the target spectrum, and $\eta_{\mathit{eff}}$ is the effective index of the waveguide for the center wavelength. The order m defines the degree of separation between the wavelength's peaks in the spectral response obtained. The relationship between the degree of separation and the order m can be defined as $\Delta_{FSR} = (\eta_{\mathit{eff}}\lambda_c)/(n_g m)$, where $n_g$ is the group index of the waveguide. For example, cascades of AMZIs can also be used to further demultiplex the input signal into smaller and smaller bandwidths until the bandwidths coincide with individual wavelengths, resulting in a more accurate interference pattern.

The process by which the spectrum of the interference signal is analysed and the spectral content delivered to the output image processor 223 is the same as previously described.

The 2×2 variable coupler 205 allows for a coupling ratio adjustment of the splitting of the initial photonic input signal from the broadband light source 201. As explained previously, the split is preferably and approximately equal, whereby each split signal contains 50% of the power of the initial input signal. In practice, a 50% split can be difficult to achieve and may not be essential, with a greater proportion passing to the imaging optics (which is a more lossy path) and a lesser proportion to the reflector. The 2×2 variable coupler 205 allows the split to be pre-defined and reprogrammed according to the user's preference. Thus, the split can be decided to be a 60:40 split or a 70:30 split or a 80:20 split or even a 90:10 split in favour of the image path specified by the user, and can be reprogrammed between scans and/or users. The retro reflector 211 reflects the incoming split signal with minimal scattering, therefore reducing the amount of power loss in the signal. In the spectrometer 220, the wavelength fanout 221 separates out the wavelengths of the interference signal transmitted from the variable coupler 205, thereby obtaining the spectrum of the interference signal. The detection 222 internal module then detects the spectrum obtained. Once the spectrum has been detected, it can be sent to the output image processor 223.

An advantage of providing on-chip wavelength fan-out is that additional external components that would otherwise be required for wavelength fan-out are no longer needed, therefore reducing the amount of loss in the system by negating the losses induced from the external components. The off-chip detection can be compact and have a reduced complexity with regards to the operations that the external component must perform, thus reducing the associated loss in the component while increasing reliability due to the lower number of operations that must be performed. Detection may also be incorporated and integrated onto the PIC 203 if available to the material platform, further reducing the device complexity.

The invention claimed is:

1. An apparatus suitable for optical coherence tomography (OCT) scanning of a subject, the apparatus comprising:
at least one source for providing a first signal and a reference signal;
a photonics integrated circuit comprising:
(i) a first path for receiving a reflected first signal, reflected from the subject;
(ii) a second path for coupling the reflected first signal to the reference signal to provide an interference signal, and
(iii) a variable delay for varying an optical path length of one of the reference signal and the first signal to match the optical path length of the reference signal to an optical path length of the reflected first signal, wherein the variable delay comprises a series of binary switches and a series of path elements of different lengths of L wherein the series of path elements comprises lengths of L up to $2^N$ L, where N is a positive integer; and
a detector for analyzing and detecting the interference signal.

2. The apparatus of claim 1, wherein the variable delay is a binary delay implementing a delay, in steps of L, of 0 to $(2 \times 2^N - 1)$ L.

3. The apparatus of claim 2, wherein the variable delay has N delay path elements and N+1 binary switches, one binary switch before each delay path element, to selectively switch between a direct path or the delay path element, and one binary switch at the output to selectively switch from the direct path or a final delay path element to an output of the variable delay.

4. The apparatus of claim 2, wherein the switches are two-way multiplexing or demultiplexing switches.

5. The apparatus of claim 1, wherein the variable delay acts on the reference signal.

6. The apparatus of claim 1, wherein one of the paths of different lengths includes a tunable labyrinth with integrated phase shifter.

7. The apparatus of claim 1, wherein the at least one source comprises a broadband light source and the detector for analyzing and detecting the interference signal comprises a spectrometer.

8. The apparatus of claim 7, wherein the spectrometer is implemented as one of an arrayed waveguide grating, AWG, a ring bus, a ring fan-out, a binary asymmetric Mach-Zehnder interferometer (AMZI), or an AMZI fan out.

9. The apparatus of claim 1, wherein the at least one source a swept laser source and the detector comprises a point photodetector.

10. The apparatus of claim 1, wherein the at least one source comprises a beam-splitter, and wherein the beam-splitter beam-splits the first signal.

11. The apparatus of claim 1, wherein the second path is a 2×2 coupler, and wherein the 2×2 coupler is one of a directional coupler, a multimode interferometer or a Mach-Zender interferometer.

12. The apparatus of claim 1, wherein the photonic integrated circuit comprises:
a first path for guiding the first signal to a set of imaging optics to the subject and for guiding reflected light from the subject back through the set of imaging optics to the second path for coupling the reflected first signal to the reference signal to provide an interference signal; and
a second path for guiding the reference signal to a reflector and back to the second path for coupling the reflected first signal to the reference signal to provide an interference signal.

13. The apparatus of claim 12, wherein the first and second paths comprise polarization-maintaining fibers for maintaining polarization of the first signal and the reference signal respectively.

14. The apparatus of claim 1, further comprising an output image processor for remote viewing of the analyzed interference signal an on-chip control unit for remote control of the variable delay.

15. The apparatus of claim 1 wherein the minimum value of N is 2.

16. A method suitable for performing an optical coherence tomography (OCT) scan, the method comprising:
providing a first signal provided by a light source;
providing a reference signal;
reflecting the first signal from a subject and coupling the reflected first signal to the reference signal to provide an interference signal;
adjusting a delay of one of the reference signal and the first signal by a variable delay to match an optical path length of the reference signal to an optical path length of the reflected first signal, wherein the step of adjusting comprises selecting between paths of different lengths, wherein the variable delay comprises a series of binary switches and a series of different selectable path elements, wherein the series of path elements comprise lengths of L up to $2^N L$, where N is a positive integer; and
analyzing the interference signal.

17. The apparatus of claim 16 wherein the minimum value of N is 2.

* * * * *